US009795279B2

(12) United States Patent
Hogrefe et al.

(10) Patent No.: US 9,795,279 B2
(45) Date of Patent: Oct. 24, 2017

(54) ENDOSCOPE COUPLER (71) Applicant: Access Optics, LLC, Broken Arrow, OK (US)

(72) Inventors: Robert H. Hogrefe, Broken Arrow, OK (US); Thomas Mayer, Muskogee, OK (US); John Hannam, Broken Arrow, OK (US)

(73) Assignee: Access Optics, LLC, Broken Arrow, OK (US)

( * ) Notice: Subject to any disclaimer, the term of this patent is extended or adjusted under 35 U.S.C. 154(b) by 294 days.

(21) Appl. No.: 14/518,661

(22) Filed: Oct. 20, 2014

(65) Prior Publication Data

US 2015/0112137 A1  Apr. 23, 2015

Related U.S. Application Data (60) Provisional application No. 61/893,733, filed on Oct. 21, 2013.

(51) Int. Cl.
*A61B 1/00* (2006.01)
*A61B 1/04* (2006.01)

(52) U.S. Cl.
CPC ........ *A61B 1/00121* (2013.01); *A61B 1/0011* (2013.01); *A61B 1/00126* (2013.01); *A61B 1/00188* (2013.01); *A61B 1/042* (2013.01)

(58) Field of Classification Search
CPC ....... A61B 1/00121; A61B 1/042; A61B 1/04; A61B 1/00188; A61B 1/0126; A61B 1/0011; A61B 1/00105
See application file for complete search history.

(56) References Cited

U.S. PATENT DOCUMENTS

| 4,624,243 | A | * | 11/1986 | Lowery ............ A61B 1/00165 600/114 |
|---|---|---|---|---|
| 4,655,569 | A | | 4/1987 | Sims |
| 4,740,058 | A | | 4/1988 | Hori et al. |
| 5,368,014 | A | | 11/1994 | Anapliotis et al. |
| 5,377,669 | A | | 1/1995 | Schulz |
| 5,396,366 | A | | 3/1995 | Brown et al. |
| 5,575,757 | A | | 11/1996 | Kennedy et al. |
| 5,682,199 | A | | 10/1997 | Lankford |
| 5,772,355 | A | | 6/1998 | Ross et al. |
| 5,792,045 | A | | 8/1998 | Adair |
| 5,868,665 | A | | 2/1999 | Biggs |
| 6,069,651 | A | | 5/2000 | Tsuyuki et al. |

(Continued)

FOREIGN PATENT DOCUMENTS

| CN | 201438253 | 4/2010 |
|---|---|---|
| EP | 0845694 | 6/1998 |

OTHER PUBLICATIONS

Print-off from website of Serwell Medi-Equip (P) Ltd. regarding Digital CCD Camera for Endoscope.

(Continued)

*Primary Examiner* — Timothy J Neal (57) ABSTRACT

An endoscope coupler with a split focus ring having direct engagement between the focus ring and the lens cell. The endoscope coupler may also have a changeable lens cartridge which can be replaced when moisture penetrates and ruins a the previous lens cartridge. Additional features may include branding security key which prevents use of replacement parts from third parties.

26 Claims, 6 Drawing Sheets

(56) References Cited

U.S. PATENT DOCUMENTS

| | | |
|---|---|---|
| 6,572,537 B2 | 6/2003 | Futatsugi et al. |
| 6,716,161 B2 | 4/2004 | Higuma et al. |
| 6,767,322 B1 | 7/2004 | Futatsugi et al. |
| 6,932,760 B1 | 8/2005 | Pang et al. |
| 7,063,663 B2 | 6/2006 | Kazakevich |
| 7,212,737 B2 | 5/2007 | Dehmel et al. |
| 7,387,605 B2 | 6/2008 | Frith |
| 2005/0197533 A1 | 9/2005 | May et al. |
| 2011/0018988 A1 | 1/2011 | Kazakevich et al. |
| 2013/0102846 A1 | 4/2013 | Sjostrom et al. |

OTHER PUBLICATIONS

Print-off from website of Visiscope regarding endocoupler.
Scholly Fiberoptic GMBH brochure regarding Zoom HD endokoppler.
Print-off from website of Stericam regarding endoscopic camera.

* cited by examiner

ENDOSCOPE COUPLER

FIELD OF THE INVENTION

The present invention relates generally to an endocoupler. More particularly, the present invention relates to coupler to join a camera to an endoscope.

BACKGROUND OF THE INVENTION

Endoscopes are commonly used in medical procedures. They provide a surgeon with a view of internal organs, muscle, tendons and other tissue and allow the surgeon to perform various medical procedures with minimum intrusion and scarring.

An endoscope coupler or endocoupler is used to optically and physically connect an endoscope to a camera. The camera can be used to capture the image on the endoscope and transmit it for viewing on a screen and/or record the procedure. This provides a larger and easier viewed image for the surgeon during the procedure.

During the procedure the endocoupler is in close proximity to the entry point of the endoscope into the patient's body. This means the endocoupler must be sterile for safe use. Sterilization can be accomplished by running the endocoupler through an autoclave or through a sterilizing bath. Either way the endocoupler and must be water tight and capable of withstanding the sterilization process. If moisture penetrates the lens assembly it ruins the clarity of the image passing through it. Thus the endocoupler must be extremely rugged.

Prior art endocouplers have relied on complex construction to provide the needed water tight and rugged device. Many use a complicated magnet drive to focus the optical train. However such mechanisms are expensive to manufacture and susceptible to wear and tear. Further the optical train in these devices is not replaceable. Therefore what is needed is an endocoupler that is rugged enough to survive multiple sterilization cycles. The endocoupler must also be a simple design that is inexpensive to manufacture and maintain.

Further, the optical trains on prior art endocouplers rely on windows sealed to the body of the optical train. These windows do not provide any magnification of the image. Rather magnification is provided by additional lens located between the two sealing windows. This adds additional cost to the optical train. What is needed is an endocoupler design that eliminates extra windows in the optical train.

BRIEF SUMMARY OF THE INVENTION

The present invention is an improved endocoupler. It has a simplified design that reduces the number of parts and simplifies manufacture, operation and maintenance. The focus mechanism provides direct engagement between the focus ring and lens cell. It provides movement for focusing of an image without rotation of the lens cell.

The lens cell also has a replaceable lens cartridge. Thus the endocoupler of the present invention may be reused if moister penetrates the lens cartridge and causes condensate on the lens. This is accomplished by simply replacing the lens cartridge with a new lens cartridge.

Construction of the lens cell is simplified by using the lenses as the external cell windows. The lenses are bonded to the ends of the lens cell by means known in the art to create hermetic ceramic to metal seals.

The endocoupler also has improved coupling mechanism that provides engagement between the base and an endoscope. This engagement is achieve with minimal movement of the parts of the base. Construction of the coupler is further simplified by use of the split focus ring.

BRIEF DESCRIPTION OF THE DRAWINGS

Preferred embodiments of the invention will now be described in further detail. Other features, aspects, and advantages of the present invention will become better understood with regard to the following detailed description, appended claims, and accompanying drawings (which are not to scale) where:

DETAILED DESCRIPTION OF THE PREFERRED EMBODIMENT(S)

Figure 1:
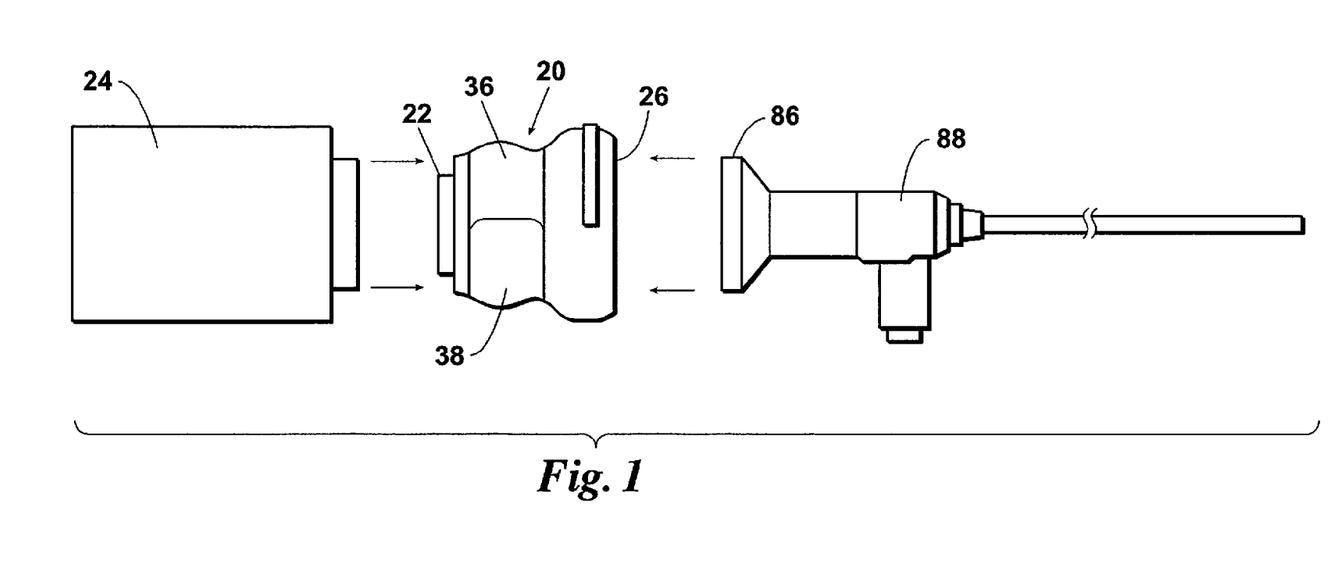
FIG. 1 is a schematic view of the endocoupler with an endoscope and camera.
Figure 2:
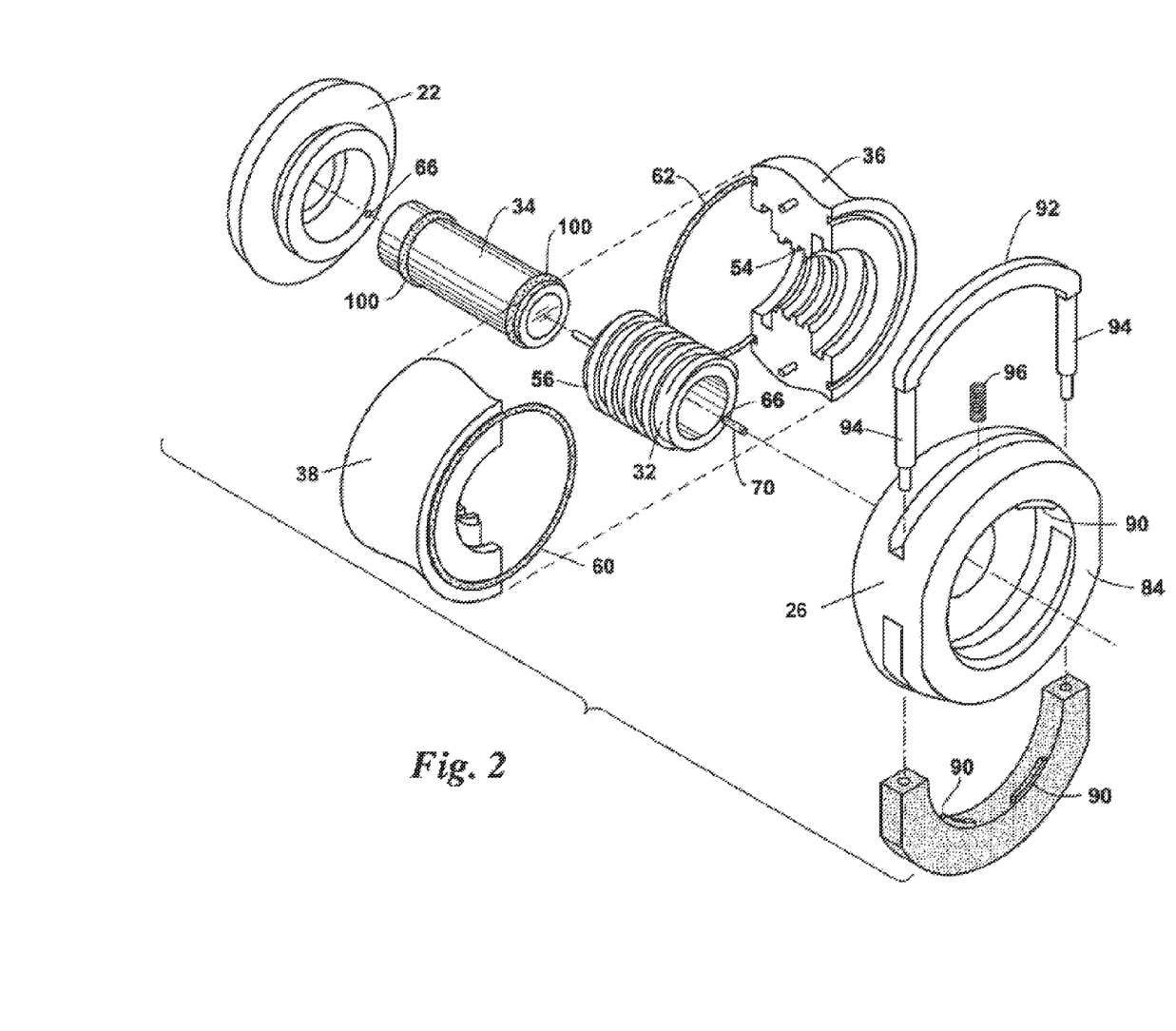
FIG. 2 is an exploded view of the preferred embodiment of the present invention.

Turning now to the drawings wherein like reference characters indicate like or similar parts throughout, FIG. 1 shows how the coupler would be used, FIG. 2 illustrates an exploded view of the endocoupler 20. Details of the construction of the various parts making up the endocoupler may be better illustrated in the other Figures. The endocoupler 20 has a first end or camera mount 22 which secures to a camera 24 by various means known in the art and a second end or base 26 which secures to an endoscope 88. The endocoupler 20 has a focus mechanism 28 which allows the user to focus and/or zoom the image from the endoscope 88 before it is captured and transmitted by the camera 24.

The focus mechanism 28 has a focus ring 30, lens cell 32, and lens cartridge 34. The focus ring 30 is generally annular in shape and is constructed from a first and second half 36 and 38, each having complementary parts that when assembled form a singular annular ring. The focus ring 30 has a groove and flange 40 on the front edge 42 and a groove and flange 44 on the rear edge 46. The groove and flange 40 on the front edge 42 inner lock with a complementary groove and flange 48 on the base 26. The groove and flange 44 on the rear edge 46 interlock with a complementary groove and flange 50 on the camera mount 22. This eliminates the need for a separate main housing. The interior surface 52 of the focus ring 30 has one or more helical or other threads or other structure 54 that interlock with complementary helical threads 56 on the exterior surface 58 of the lens cell 32. The device may also use a lever mechanism, rack and pinion, pin engaging a thread, or equivalent mechanism to achieve the linear movement of the lens cell 32. Further it would be possible to have threads on either the interior surface 52 of the focus ring 30 or the exterior 58 of the lens cell 32 and have a structure that engages with the threads on the opposing element without the threads. An O-ring 60 captured between the focus ring 30 and the base 26 provides a seal between these two pieces. Likewise a second O-ring 62 captured between the focus ring 30 and the camera mount 22 provides a seal between these two parts.

The lens cell 32 has a hollow cylindrical body 64 with one or more helical or other threads 56 located on the exterior surface 58. The interior cross section of the hollow cylindrical body 64 may have a shape other than a circle. A lens cartridge 34 is located inside the hollow cylindrical body 64. The lens cartridge 34 may be secured inside the lens cell 32 by a branding security feature or other locking mechanism. There is also an aperture 66 that runs the length of body 64 and passes through the wall 68 of the body 64. An anti-rotation pin 70 passes through the aperture 66 and extends from either end of the body 64. The first end 72 of the anti-rotation pin 70 is anchored in the camera mount 22. The second end 74 of the anti-rotation pin 70 is anchored in the base 26.

Figure 3:
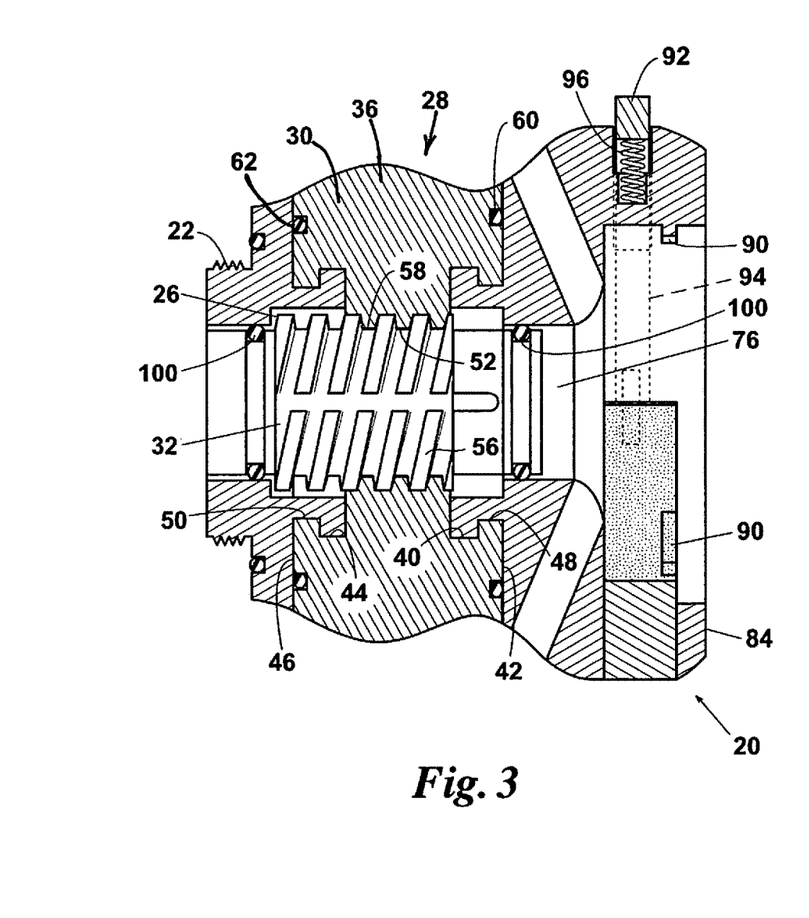
FIG. 3 is a cross section of the endocoupler with the base in the closed position.
Figure 4:
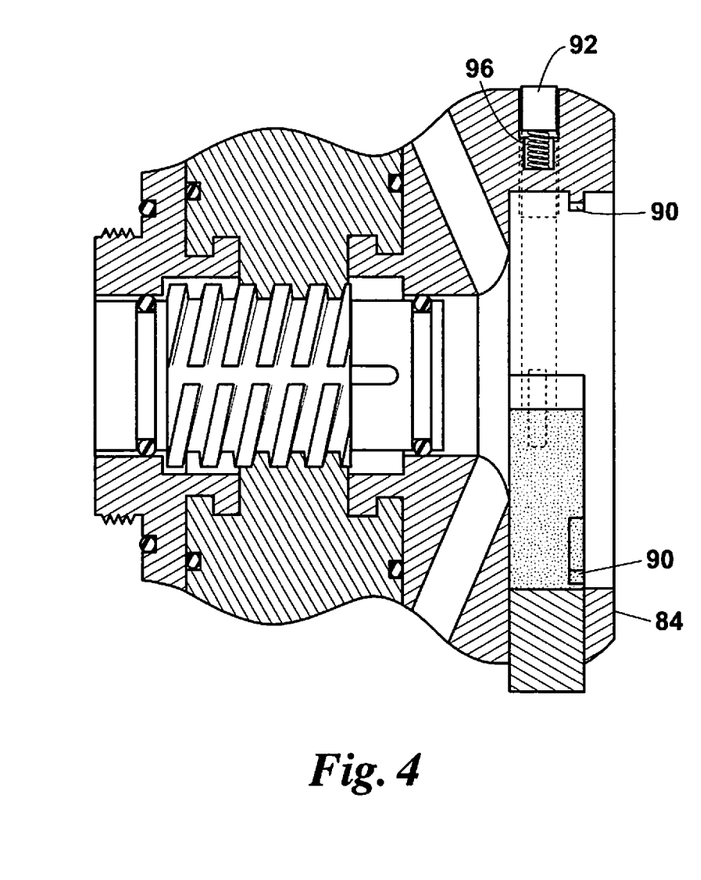
FIG. 4 is a cross section of the endocoupler with the base in the open position.

A focus chamber 76, as seen in FIGS. 3 and 4, is defined by the interior surface 52 of the focus ring 30 and the camera mount 22 on one end and the base 26 on the other end. When the focus ring 30 is rotated relative to the camera mount 24 and base 26 the engagement between the helical threads 54 of the focus ring 30 and the helical threads 56 of the lens cell 32 causes the lens cell 32 to move linearly within the focus chamber 76. As the lens cell 32 moves linearly the anti-rotation pin 70 prevents the rotation of the lens cell 32 relative to the camera mount 22 and base 26 while the anti-rotation pin 70 slides linearly along the aperture 66 in the wall 68 of the lens cell 32. The lens cell 32 can be moved linearly in either direction by rotating the focus ring 30 in either direction.

An o-ring 100 is located at each end of the focus chamber 76. They are captured between the interior surface of the focus chamber 76 and the exterior surface of the lens cartridge 34. Thus the o-rings 100 prevent debris and condensation from entering the interior of the endocoupler 20 where it might damage the mechanisms.

Figure 7:
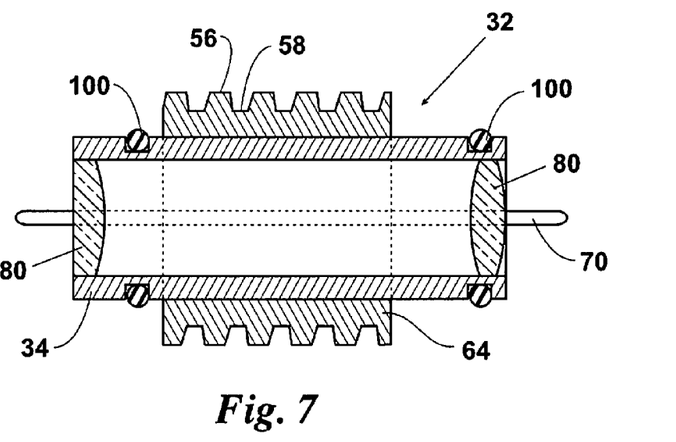
FIG. 7 is a cross section view of the lens cell and lens cartridge.
Figure 8:
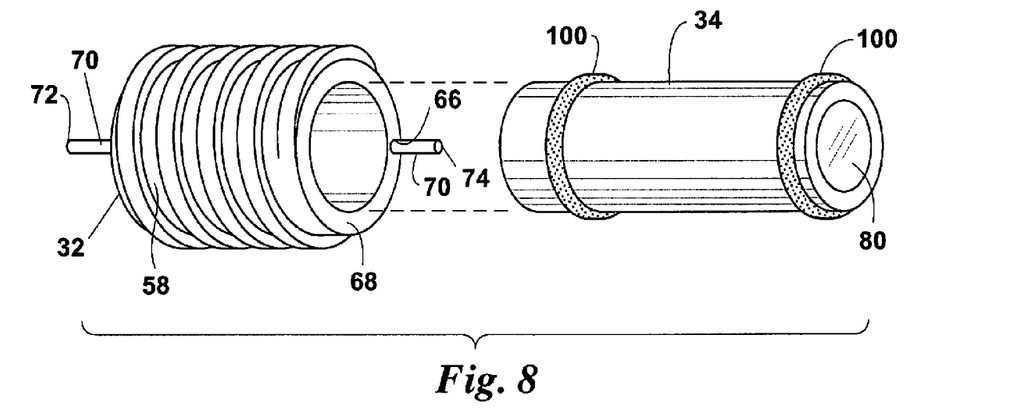
FIG. 8 is an exploded view of the lens cell and lens cartridge.

A lens cartridge 34 is sized and shaped to fit inside the body 64 of the lens cell 32. The fit between the lens cartridge 34 and the body 64 is such that the lens cartridge 34 may be removed from the body 64 of the lens cell 32 and replaced with a different lens cartridge 34. The lens cartridge 34 may be fixed in place to the body 64 by means of a mechanical locking feature and/or a temporary adhesive that can be removed when desired to allow replacement of the lens cartridge 34. Thus the endocoupler 20 may be reused if the lens cartridge 34 fails. The lens cartridge 34 may also be replaced with a lens cartridge having a different focal length or optical feature. Thus the same endocoupler 20 could be used for different application by simply replacing the lens cartridge 34.

The lens cartridge 34 preferably has a lens 80 located in each end of the cartridge. The lenses 80 are ground or otherwise formed such that they provide a magnification of an image. The lenses 80 may be sapphire, synthetic sapphire, glass, fused silica or other materials suitable for use in a lens 80. In the preferred embodiment the lenses 80 are sealed and secured to the lens cartridge 34 by methods known in the art which are capable of withstanding multiple thermal cycles in a autoclave.

Figure 5:
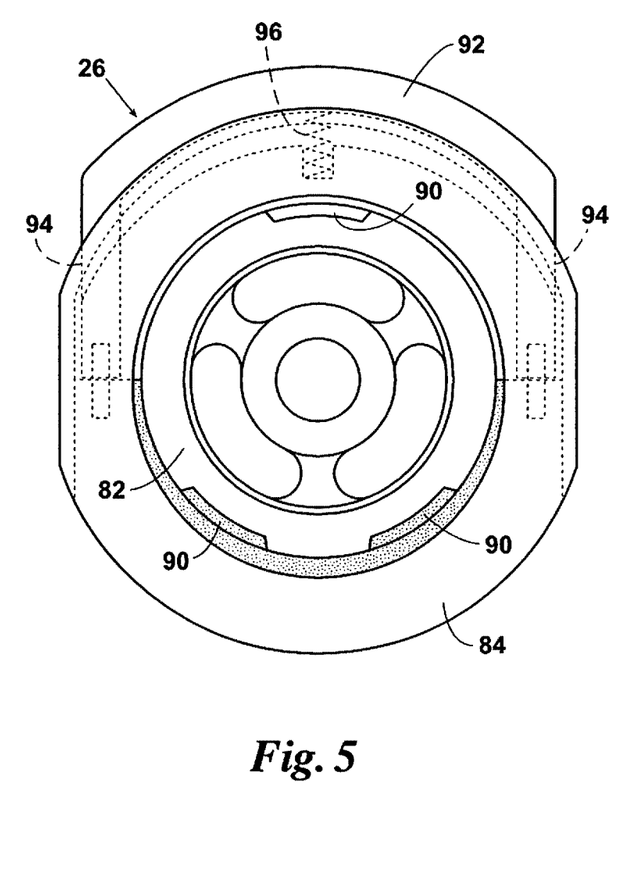
FIG. 5 is an end view of the endocoupler showing the base in the closed position.
Figure 6:
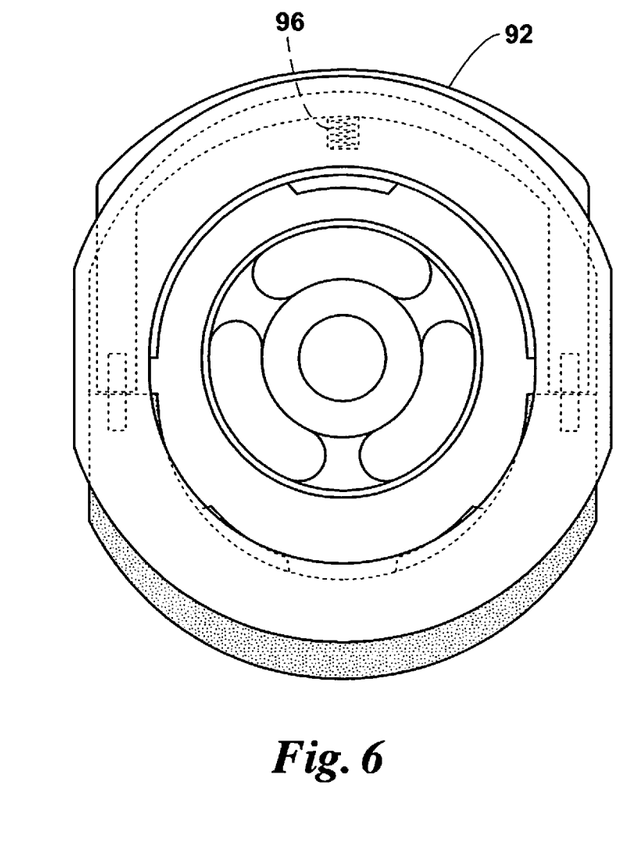
FIG. 6 is an end view of the endocoupler showing the base in the open position.

The base 26 has an opening 82 in a faceplate 84 sized to surround the end 86 of an endoscope 88. A lip 90 extends along the periphery of the opening 82 and engages the end 86 of the endoscope 88. A portion of the lip 90, preferably half of the opening 82 or less, is fixed to the face plate 84. The other portion of the lip 90, preferably half of the opening 82 or less, is linearly moveable relative to the faceplate 84. As seen in FIGS. 5 and 6 the lip 90 can take the form of short segments extending along the periphery of the opening 82.

The moveable portion of the lip 90 is mounted on each leg 94 of the yoke 92 that slidingly engages the faceplate 84 and is moveable between an open position and a closed position. The yoke 92 is biased towards a closed position. In the preferred embodiment shown in FIGS. 3-6 a leg 94 is located on each end of the yoke 92. A spring 96 located between the legs 94 of the yoke 92 and captured between the faceplate 84 and the yoke 92 provides the bias.

In order to secure the endoscope 88 to the base 26, the base 26 is opened by depressing the yoke 92. This moves a portion of the lip 90 behind the faceplate 84 thus enlarging the opening 82. The end 86 of the endoscope 88 can then be inserted into the opening 82. When the yoke 92 is released, the spring 96 moves the yoke 92 and a portion of the lip 90 to the closed position. Once in the closed position the lip 90 engages the end 86 of the endoscope 88, holding the endoscope 88 in place relative to the base 26.

Figure 9A:
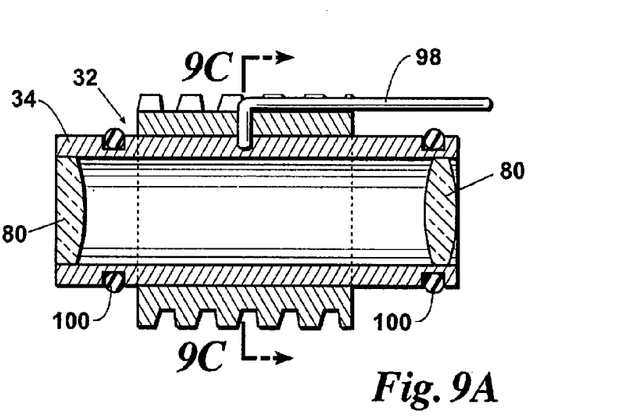
FIG. 9A is a sectional side view of the lens cell, lens cartridge and branding security feature.
Figure 9B:
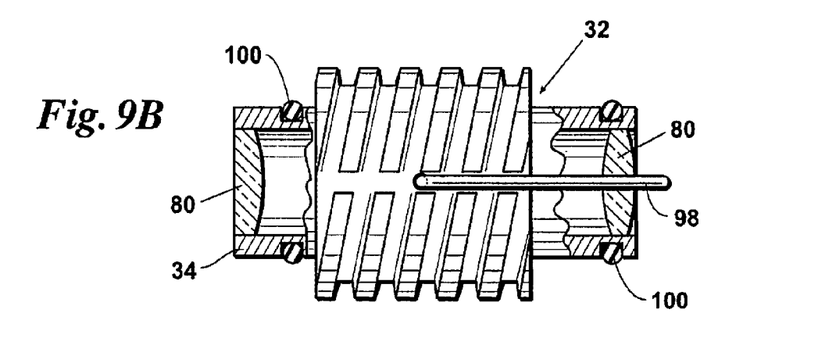
FIG. 9B is a top view partial sectional of the lens cell, lens cartridge and branding security feature.
Figure 9C:
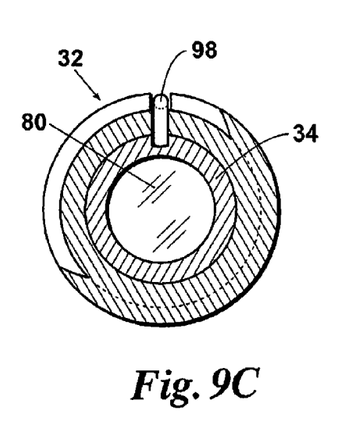
FIG. 9C is a sectional end view of the lens cell, lens cartridge and branding security feature taken along the line shown in FIG. 9A.

The branding security key may be incorporated into the pin 98 used to hold the lens cartridge 34 in place. See FIGS. 9A-9C. The branding security key ensures a replacement lens cartridge 34 from a third party cannot be used. The pin 98 could have an L shape so that the leg of the L goes into a hole that goes through the lens cell 32 contacting the lens cartridge 34. The lens cartridge 34 would have a small hole in it (not all the way through) that the L leg would fit into. It serves the purpose of locking the lens cartridge 34 in position and if the lens cell 32 did not have a feature the L leg 98 could mate with the rest of the pin would bind with the focus ring 30. If the L pin 98 is bonded into the focus ring 30 you could not close the focus ring 30 because the L pin 98 would stick out of the lens cell 32 preventing the focus ring 30 from closing. If you close the focus ring 30 the part of the L pin 98 sticking out would bind against the focus ring 30 when you tried to focus the unit. The lens cartridge 34 may also be glued in place. The feature on the lens cartridge 34 could be a indention or a groove cut around the entire tube. There may be more than one L pin 98 if needed. The length and size/shape of the L pin 98 tip may be changed to make the lens cartridge 34 specific to a customer.

There are numerous features of the present invention described above. Each of these features provide their own benefits. Thus they may be individually incorporated into a device. Likewise a plurality of these features or all of these features may be included in a device.

The foregoing description details certain preferred embodiments of the present invention and describes the best mode contemplated. It will be appreciated, however, that changes may be made in the details of construction and the configuration of components without departing from the spirit and scope of the disclosure. Therefore, the description provided herein is to be considered exemplary, rather than limiting, and the true scope of the invention is that defined by the following claims and the full range of equivalency to which each element thereof is entitled.

What is claimed is:

1. An endocoupler comprising:
a camera mount;
a base; and
a focus ring with a first half and a second half, the first and second halves being complementary in shape to one another and separable from one another; wherein the focus ring directly engages a lens cell which carries a lens cartridge and rotation of the focus ring relative to the camera mount and the base causes linear movement of the lens cell relative to the camera mount, base and focus ring.

2. The endocoupler of claim 1 further comprising the lens cartridge being removably mounted in the lens cell.

3. The endocoupler of claim 1 further comprising:
a thread on an interior surface of the focus ring;
wherein the thread engages with the lens cell.

4. The endocoupler of claim 1 further comprising:
a thread on an exterior surface of the lens cell,
wherein the thread engages with the focus ring.

5. The endocoupler of claim 1 further comprising:
an aperture passing through the lens cell; and
an anti-rotation pin with a first end and a second end passing through the aperture wherein the first end of the anti-rotation pin is anchored in the camera mount and the second end of the anti-rotation pin is anchored in the base.

6. The endocoupler of claim 1 further comprising:
a focus chamber defined by an interior surface of the focus ring, the camera mount on a first end and the base on a second end;
a first seal captured between the lens cartridge and the base; and
a second seal captured between the lens cartridge and the camera mount.

7. The endocoupler of claim 1 further comprising:
a groove and flange located on a front edge of the focus ring which engages with a groove and flange on the base; and
a groove and flange located on a rear edge of the focus ring which engages with a groove and flange on the camera mount.

8. The endocoupler of claim 1 further comprising:
a seal captured between the focus ring and the camera mount, and
a second seal captured between the focus ring and the base.

9. The endocoupler of claim 1 wherein the lens cartridge is removable from the lens cell.

10. The endocoupler of claim 1 with a branding security key, said branding security key comprising:
an L-shaped pin; and
a hole through a wall of the lens cell;
wherein the leg of the L shaped pin extends through the hole in the lens cell and contacting the lens cartridge and the body of the L shaped pin will interfere with the assembly of the focus ring if the hole is not present.

11. The endocoupler of claim 1, the base further comprising:
an opening in a faceplate, the opening sized to surround an end of an endoscope;
a lip extending along a periphery of the opening and engagable with the end of an endoscope;
a first portion of the lip being fixed to the edge of the faceplate; and
a second portion of the lip mounted on a yoke and linearly moveable relative to the faceplate;
wherein the yoke is slidingly mounted to the faceplate and biased relative to the faceplate and movement of the yoke and second portion of lip move the lip to allow passage of the end of the endoscope through the opening.

12. An endocoupler including a camera mount and a base, the endocoupler further comprising:
a focus ring including a first and a second half complementary in shape to and separable from one another, the first and second halves arranged to engage the camera mount and the base;
wherein a rotation of the focus ring relative to the camera mount and the base focuses a lens cell.

13. An endocoupler according to claim 12 further comprising:
an aperture passing through the lens cell; and
an anti-rotation pin passing through the aperture and including a first end anchored in the camera mount and a second end anchored in the base.

14. An endocoupler according to claim 12 further comprising
a groove and flange located on a front edge of the focus ring which engages with a groove and flange on the base; and
a groove and flange located on a rear edge of the focus ring which engages with a groove and flange on the camera mount.

15. An endocoupler according to claim 12 further comprising a branding security key including an L-shaped pin extending through a hole in the lens cell, contacting a lens cartridge carried by the lens cell, and interfering with the focus ring if the hole is not present.

16. An endocoupler according to claim 12 further comprising the focus ring including threads on an interior surface of the focus ring.

17. A focus ring for an endoscopic coupler including a camera mount and a base, the focus ring comprising:
at least two pieces complementary in shape to and separable from one another, the
focus ring arranged to engage the camera mount and the base;
wherein a rotation of the focus ring relative to the camera mount and the base focuses a lens cell.

18. A focus ring according to claim 17 further comprising threads on an interior surface of the focus ring.

19. A focus ring according to claim 17 further comprising a focus chamber defined by an interior surface of the focus ring, the camera mount on a first end and the base on a second end.

20. A focus ring according to claim 17 further comprising:
a groove and flange located on a front edge of the focus ring which engages with a groove and flange on the base; and
a groove and flange located on a rear edge of the focus ring which engages with a groove and flange on the camera mount.

21. An endoscopic coupler comprising:
a camera mount;
a base; and
a focus ring connected at one end to the camera mount and at another end to the base and arranged to engage a lens cell;
wherein rotation of the focus ring relative to the camera mount and the base causes movement of the lens cell relative to the camera mount, the base, and the focus ring; and wherein the focus ring includes two or more complementary shaped, separable pieces.

22. An endocoupler according to claim 21 further comprising the focus ring including threads on an interior surface of the focus ring.

23. An endocoupler according to claim 21 wherein the movement of the lens cell is a linear movement.

24. An endocoupler comprising:
a camera mount;
a base; and
a focus ring connected at one end to the camera mount and at another end to the base and arranged to engage a lens cell;
wherein rotation of the focus ring relative to the camera mount and the base causes movement of the lens cell relative to the camera mount, the base, and the focus ring;
an aperture passing through the lens cell; and
an anti-rotation pin passing through the aperture and including a first end anchored in the camera mount and a second end anchored in the base.

25. An endocoupler comprising
a camera mount;
a base; and
a focus ring connected at one end to the camera mount and at another end to the base and arranged to engage a lens cell;
wherein rotation of the focus ring relative to the camera mount and the base causes movement of the lens cell relative to the camera mount, the base, and the focus ring;
a groove and flange located on a front edge of the focus ring which engages with a groove and flange on the base; and
a groove and flange located on a rear edge of the focus ring which engages with a groove and flange on the camera mount.

26. An endocoupler comprising
a camera mount;
a base; and
a focus ring connected at one end to the camera mount and at another end to the base and arranged to engage a lens cell;
wherein rotation of the focus ring relative to the camera mount and the base causes movement of the lens cell relative to the camera mount, the base, and the focus ring;
a branding security key including a pin extending through a hole in the lens cell, contacting a lens cartridge carried by the lens cell, and interfering with the focus ring if the hole is not present.

* * * * *